US006483588B1

United States Patent
Graefe et al.

(10) Patent No.: US 6,483,588 B1
(45) Date of Patent: Nov. 19, 2002

(54) ARRANGEMENT FOR DETECTING BIOMOLECULAR REACTIONS AND INTERACTIONS

(75) Inventors: Dieter Graefe, Jena (DE); Gunther Elender, Fuerstenzell (DE); Wolfgang Grau, Stadtroda (DE); Hans-Juergen Dobschal, Kleinromstedt (DE); Guenter Berthel, Jena (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 09/344,650

(22) Filed: Jun. 25, 1999

(30) Foreign Application Priority Data

Jun. 26, 1998 (DE) .......................................... 198 28 547

(51) Int. Cl.[7] .......................... G01N 21/00; G01N 21/55
(52) U.S. Cl. ....................................................... 356/436
(58) Field of Search ........................ 356/496, 491–492, 356/451, 436–440, 445

(56) References Cited

U.S. PATENT DOCUMENTS 5,999,262 A * 12/1999 Dobshal et al.

FOREIGN PATENT DOCUMENTS

DE 195 44 253 A1 5/1997

OTHER PUBLICATIONS

English Abstract of DE 195 44 253 A1.

* cited by examiner

Primary Examiner—Frank G. Font
Assistant Examiner—Amanda Merlino
(74) Attorney, Agent, or Firm—Reed Smith LLP

(57) ABSTRACT

An arrangement for the detection of biomolecular reactions and interactions using the RS screening method and comprises a specimen plate or microtiter plate (PP or MTP), a white light source with subsequently arranged illumination beam path, a splitter plate on which the PP or the MTP is set for generating a detection beam path, and optical means for imaging the measurement beam path and reference beam path on a spatially resolving detector array of a CCD camera which is connected with an evaluating unit or with a computer for determining measurement values. The arrangement particularly provides optical imaging elements for imaging the measurement beam path and reference beam path at different positions on the detector array of the CCD camera simultaneously and without overlap, a monochromator which comprises a plurality of interference filters and which is arranged subsequent to the light source in the illumination beam path; a component assembly which collimates the illumination beam path, is formed of optical elements and is arranged between the monochromator and the splitter plate; and specimen plate or microtiter plate, and an optical imaging element for complete spatial separation of the measurement beam path and reference beam path in, or in the vicinity of, an intermediate inage plane or aperture diaphragm plane.

15 Claims, 4 Drawing Sheets

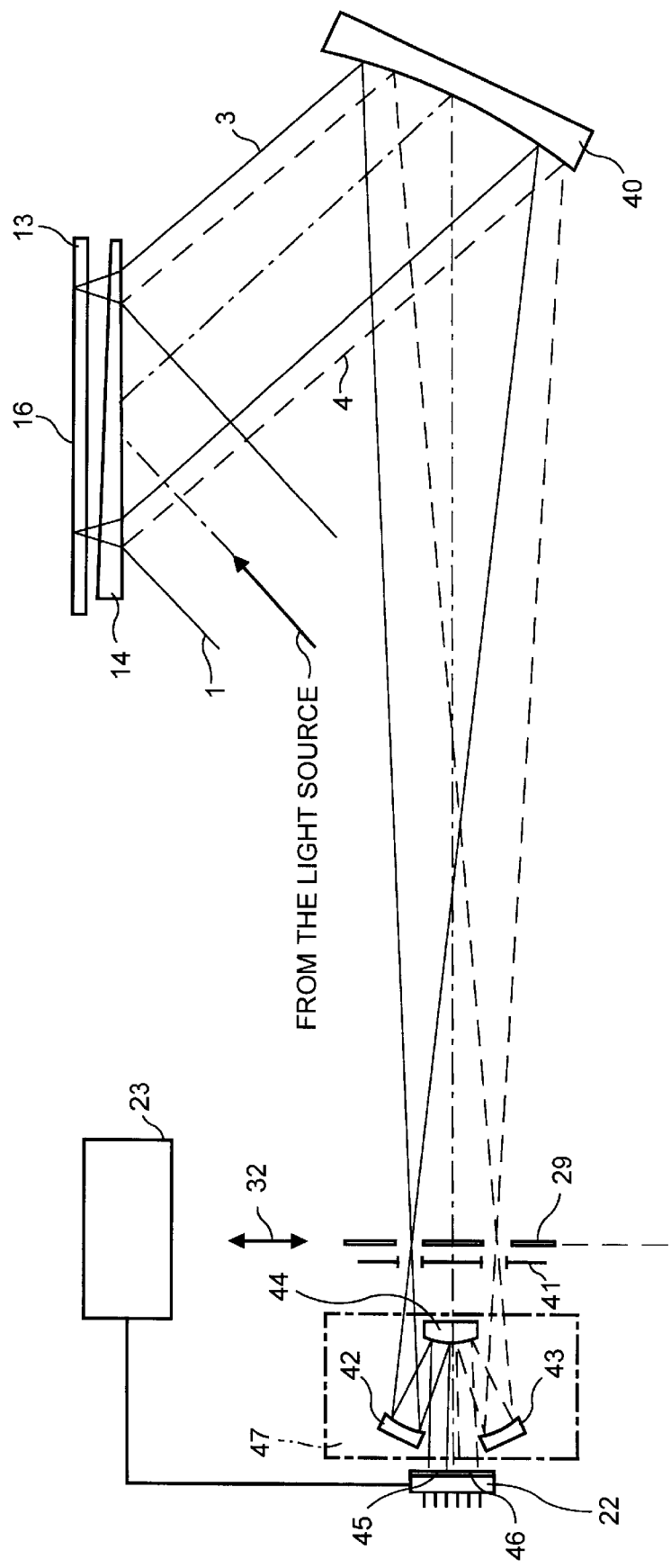
F I G. 4

ARRANGEMENT FOR DETECTING BIOMOLECULAR REACTIONS AND INTERACTIONS

BACKGROUND OF THE INVENTION a) Field of the Invention

The invention is directed to an arrangement for detecting biomolecular reactions and interactions according to the method of reflectometric interference spectroscopy (RS screening method).

b) Description of the Related Art

A process and a device for the detection of physical, chemical, biochemical and biological reactions and interactions are known from DE 196 15 366 A1. In this way, the interactions of biomolecules with biofunctionalized layers in liquid phase are detected in a large number of samples simultaneously by white light interference. Essential parameters for this measurement technique are the detection of the smallest binding detectable with certainty and the stability of this output signal over the binding time span. In the device described herein for carrying out the method, a large number of specimens arranged on a substrate plate or microtiter plate are illuminated with light from a light source via an illumination beam path in which are arranged, among others, a collimator, monochromator and polarizer. The substrate plate or microtiter plate is arranged on a wedge-shaped carrier plate by which a measurement beam path and a reference beam path are generated and imaged on a detector array of a CCD camera via optical elements arranged downstream.

Further, this reference shows that a switchable diaphragm is provided in a focal plane in which the measurement beam path and reference beam path are imaged, wherein these two beam paths can be alternately imaged on the detector array by the switchable diaphragm. In addition, the two above-mentioned beam paths are imaged at the same location on the detector array through a deflecting prism in the reference beam path, so that different sensitivities of the pixel-form receiver elements of the array are referenced out. With this switchable diaphragm, it is only possible to image the measurement beam path and reference beam path on the array at different times; however, short-term variations in light intensity and beam direction of the light source and variations in the spectral transmission characteristic of the monochromator in particular are not eliminated, which could lead to significant measurement uncertainty.

OBJECT AND SUMMARY OF THE INVENTION

Therefore, it is the primary object of the invention to provide an arrangement for the detection of biomolecular reactions and interactions in which the above-mentioned variations and their effects on measurements are extensively eliminated by means of suitable component assemblies and a suitable referencing concept.

According to the invention, this object is met in an arrangement for the detection of biomolecular reactions and interactions using the RS screening method comprising a specimen plate or microtiter plate for receiving the specimens to be examined, a white light source with subsequently arranged illumination beam path for illuminating the specimens, a splitter plate on which the specimen plate or the microtiter plate is set for generating a detection beam path formed of the measurement beam path and reference beam path, and optical means for imaging the measurement beam path and reference beam path on a spatially resolving detector array of a CCD camera which is connected with an evaluating unit or with a computer for determining measurement values. The arrangement further provides optical imaging elements for imaging the measurement beam path and reference beam path at different positions on the detector array of the CCD camera simultaneously and without overlap, a monochromator which comprises a plurality of interference filters and which is arranged subsequent to the light source in the illumination beam path and a component assembly which collimates the illumination beam path. The component assembly is formed of optical elements and is arranged between the monochromator and the splitter plate and specimen plate or microtiter plate. An optical imaging element is also included for complete spatial separation of the measurement beam path and reference beam path in, or in the vicinity of, an intermediate image plane or aperture diaphragm plane.

Accordingly, it is advantageous when a switchable closure unit is arranged in, or in the vicinity of, the intermediate image plane or aperture diaphragm plane. This makes it possible to record dark references by blocking the measurement beam path and reference beam path and accordingly to eliminate the influence of extraneous light on the measurements.

Further, it is advantageous when the additional optical imaging elements used for separate simultaneous imaging of the measurement beam path and reference beam path are arranged in, or in the vicinity of, the aperture diaphragm plane of the detector beam path comprising these two beam paths.

In accordance with a further embodiment form of the invention, a shared optical imaging element, for example, a lens comprehending both beam paths, is provided for imaging the measurement beam path and reference beam path on the receiver array of the CCD camera. In order to achieve a separation of the measurement beam path and reference beam path in the plane of the detector such that the measurement beam path and reference beam path are free from overlap, at least one deflecting element, each in the form of a deflecting prism, for example, is arranged in front of the optical imaging element in the direction of light in each of these beam paths.

Another advantageous embodiment form of the invention results when the measurement beam path and reference beam path each have their own optical imaging element for spatially separated imaging of these beam paths on the receiver array. This imaging element can be, for example, a lens or also an optical imaging system comprising a plurality of lenses.

According to another feature of the invention, the monochromator which is provided in the illumination beam path subsequent to the polychromatic light source in the direction of light comprises a switchable filter disk in which are arranged a plurality of interference filters. It has turned out in practice that a high detection accuracy can be achieved when working according to the RS method even with a small quantity of spectral channels, so that the evaluation of measurements is significantly simplified. Work can already be carried out successfully with at least three different interference filters, i.e., in three spectral channels. It has proven advantageous to work with six to eight spectral channels, that is, also with an equal number of interference filters. In measurements of changes brought about by the bound specimens in the layer thickness of a suitable polymer film applied to the specimen plate, the spectral channels form the criterion for these measurements to a certain extent. The adjusting accuracy and the stability of the spectral position of the interference extrema and their distance from one another are essential criteria for the selection of the monochromator. Ideally, these criteria are met by interference filter monochromators. In addition, there is the high light-conducting value of these monochromators which is important in the case of large-area illumination of specimen plates or microtiter plates.

In principle, grating monochromators could also be used in the illumination beam path. However, these grating monochromators are disadvantageous, for one, in that they have substantially lower light efficiency compared with interference monochromators. Accordingly, it is also advantageous when a wedge-shaped splitter plate is provided, whose at least one optically active surface has an antireflection coating. With respect to a plane-parallel splitter plate, it is also advantageous when at least one of the optically active surfaces of this splitter plate is provided with an antireflection coating.

When using a plane-parallel plate as beam splitter, the latter must be arranged in the beam path in such a way that it encloses an angle, preferably a small angle, with the specimen plate or microtiter plate carrying the specimens. surface of the plane-parallel plate which is not used for generating the reference beam path is provided with an antireflection coating. The other surface of the plate is advantageously provided with a partially reflecting layer in such a way that a balancing of the reflected intensities in the measurement beam path and reference beam path is achieved over the utilized spectral range.

In another embodiment form of the arrangement according to the invention, the optical elements collimating the illumination beam path and/or the optical imaging elements for imaging the measurement beam path and reference beam path in the aperture diaphragm plane or intermediate image plane and/or the additional optical imaging elements for imaging this aperture diaphragm plane or intermediate image plane on the spatially resolving detector array of the CCD camera are imaging reflectors. It is accordingly advantageous when the optical imaging elements for imaging the measurement beam path and reference beam path in the aperture diaphragm plane or intermediate image plane and/or the additional optical imaging elements for imaging this aperture diaphragm plane or intermediate image plane on the spatially resolving detector array of the CCD camera are convex and concave and/or plane reflectors.

The chromatic aberrations in imaging are minimized to a great extent through the use of reflecting imaging elements such as mirror optics in the form of concave mirrors.

The invention will be described more fully in the following.

BRIEF DESCRIPTION OF THE INVENTION

In the drawings:

FIG. 4 shows an arrangement with reflectors as imaging optical elements.

DESCRIPTION OF THE PREFERRED EMBODIMENTS

Figure 1:
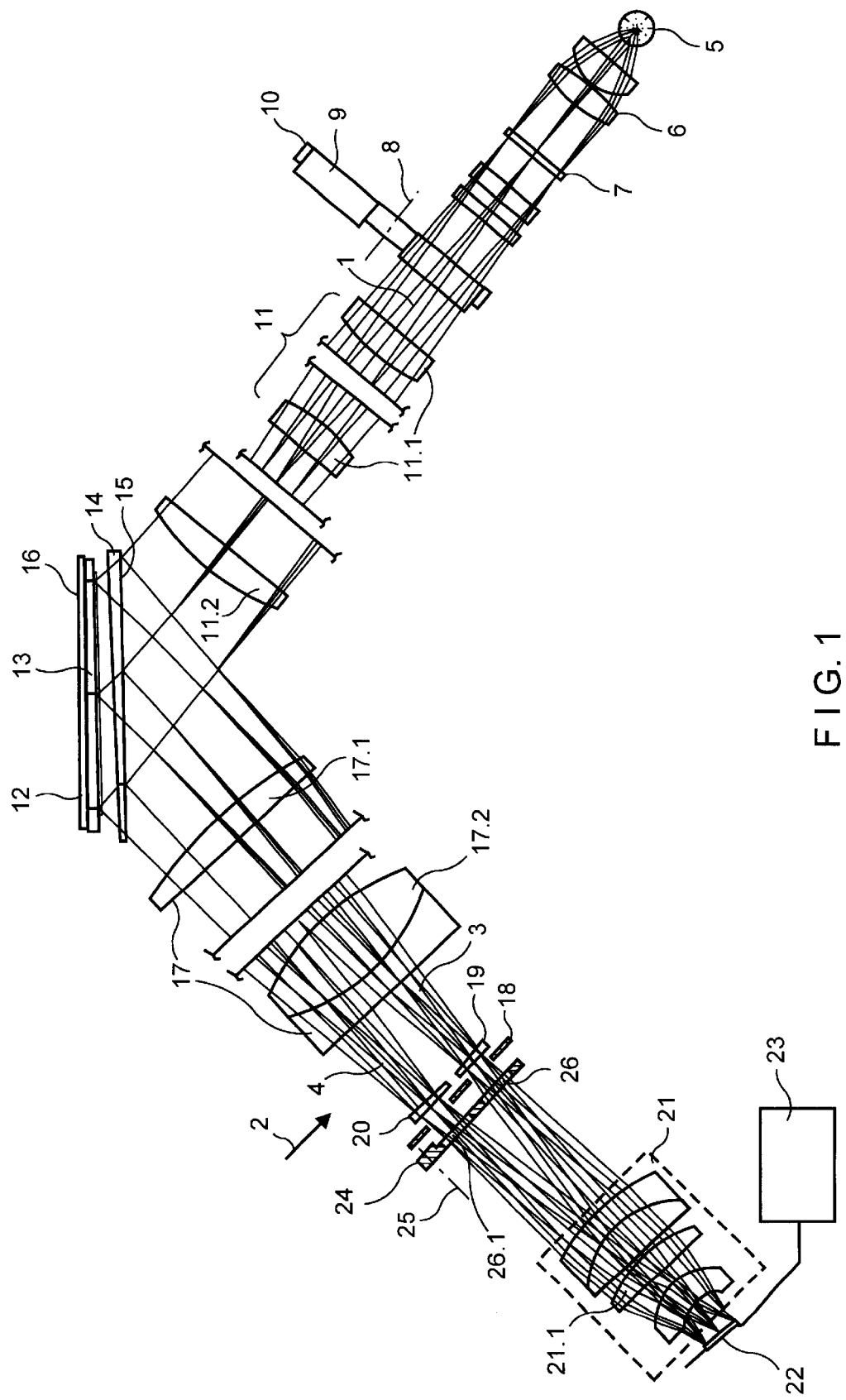
FIG. 1 shows the beam path of an arrangement according to the invention with an optical imaging system in the detection beam path with a shared objective.

FIG. 1 shows the beam path of the arrangement for detecting biomolecular reactions and interactions according to the RS screening process, wherein details of construction have been left out. The individual structural component parts and component assemblies are shown in a highly schematic manner. An illumination beam path 1 and a detection beam path 2 are provided in the arrangement, wherein the detection beam path 2 comprises a measurement beam path 3 and a reference beam path 4. A polychromatic light source 5 is arranged in the illumination beam path 1, immediately followed, considered in the direction of light, by a collimator 6 and a polarizer 7, e.g., in the form of a polarization filter. An interference monochromator with a filter disk 10 which is displaceable about an axis 8 and comprises a plurality of interference filters 9 is provided, as monochromator, downstream of the polarizer 7 in the part of the illumination beam path I that is directed in parallel manner through the collimator 6. This interference filter monochromator is outfitted with at least three different interference filters 9; it has proven advantageous in practice to work with six to eight spectral channels and with the same number of interference filters 9 for a high accuracy in measurements with relatively little expenditure on technology and in a relatively economical manner. In principle, however, more interference filters 9 can also be used.

The filter disk 10 is followed by a component assembly 11 which has a plurality of optical members 11.1 and 11.2 making up a telescopic system and generates a parallel beam path for illuminating the microtiter plate or specimen plate 13 carrying the specimens. This specimen plate 13 has a carrier layer 12 formed of a suitable polymer, the specimens (not shown) being arranged thereon. A wedge-shaped splitter plate 14 which has a partially reflecting surface 15 on the light source side is arranged forward of this specimen plate 13. The reference beam path 4 is generated on this partially coated surface 15 by reflection. The light passing through the splitter plate 14 impinges on the surface 16 of the specimen plate 13 carrying the specimens and is reflected on this surface 16 so as to be influenced by the specimens arranged thereon and forms the measurement beam path 3. The measurement beam path 3 and reference beam path 4 are then focused in an aperture diaphragm plane 18 through an imaging system 17 comprising optical imaging elements 17.1; 17.2, wherein a deflecting prism 19 and 20, respectively, serving to spatially separate the measurement beam path 3 and reference beam path 4 is arranged in, or in the vicinity of, the aperture diaphragm plane 18 corresponding to the two beam paths 3 and 4. Instead of these deflecting prisms 19; 20, reflectors can also be provided in a suitable arrangement for separation and imaging of the measurement beam path and reference beam path. An example for a construction of this kind is described hereinafter with reference to FIG. 4. The image of the surface 16 carrying the specimens or of the underside of a utilized microtiter plate as measurement beam path 3 and, next to it, the image of the reference beam path 4 are generated by a subsequently arranged objective 21 comprising optical elements 21.1 on a spatially resolving detector array 22 of a CCD camera, known per se, which is connected with an evaluating unit or with a computer 23, which detector array 22 comprises CCD elements. The deflecting prisms 19 and 20 spread the associated beam paths 3 and 4 apart to the extent that the images of the measurement beam path 3 and reference beam path 4 are separated from one another in the plane of the detector array 22 far enough to prevent mutual overlapping. These two beam paths 3 and 4 are simultaneously imaged on the detector array 22. The electric measurement signals generated by the detector array 22 are processed in the computer 23 to obtain corresponding measurement values characterizing the biomolecular reaction or interaction or the bond to be analyzed.

Further, in the arrangement shown in FIG. 1, a closure 24 is provided in, or in the vicinity of, the aperture diaphragm plane 18, by means of which the measurement beam path 3 and reference beam path 4 can be blocked or released. A step of this kind is required in order to carry out dark measurement and to obtain a dark signal needed for correction or calibration purposes and which can be used for correcting the measurement values.

For the sake of simplicity, this closure 24 is shown in FIG. 1 as a disk with openings 26 and 26.1 which is rotatable about an axis 25 and can be swiveled out of the detector beam path 2 when this beam path is to be interrupted and imaging is not to be carried out on the detector array 22. However, other suitable constructions for interrupting the detector beam path are possible.

Figure 2:
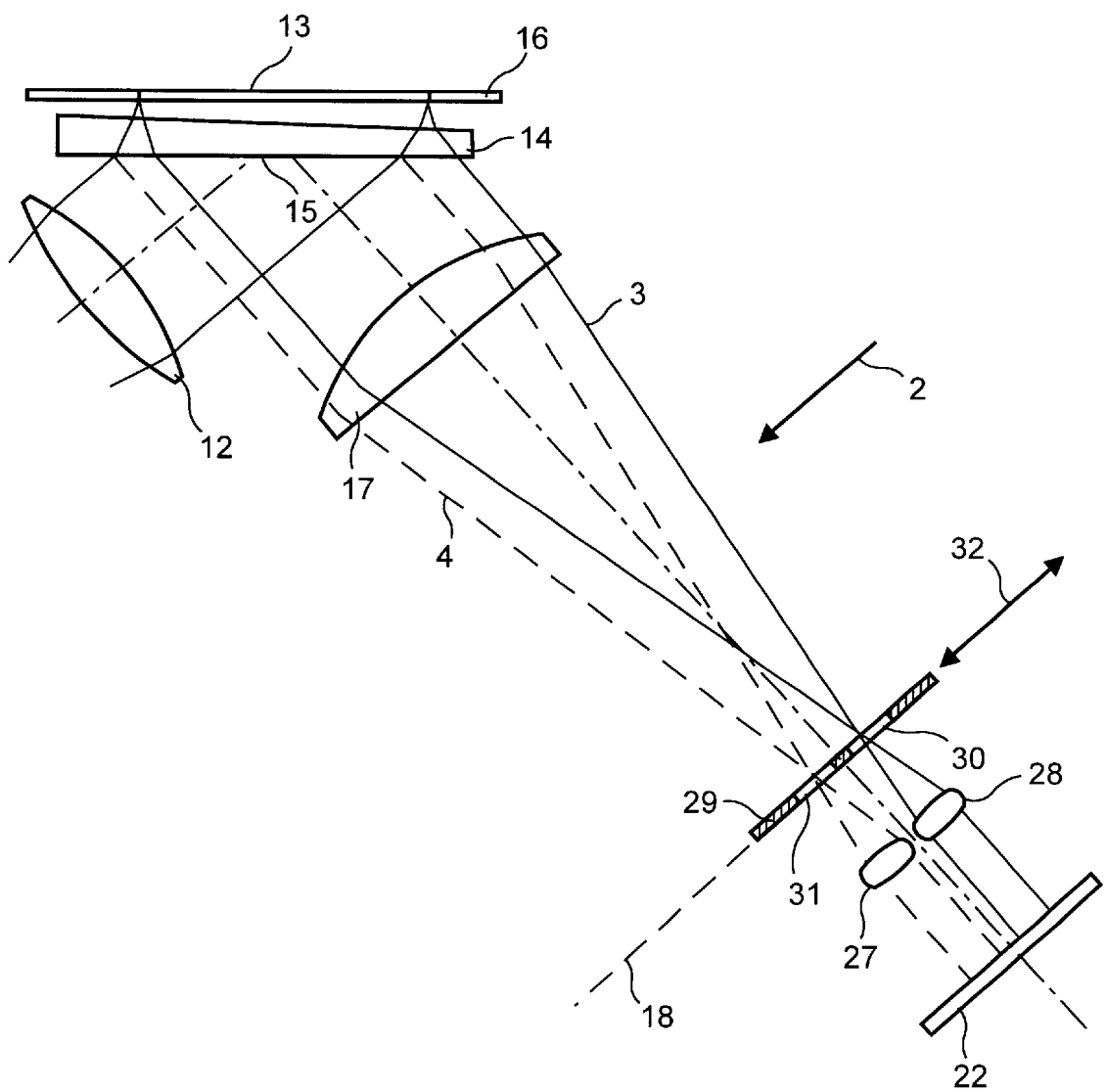
FIG. 2 shows an optical imaging system in the detection beam path with two separate imaging objectives.

An arrangement in which the two beam paths (measurement beam path 3 and reference beam path 4) imaged in, or in the vicinity of, the aperture diaphragm plane 18 are imaged on the detector array 22 by two separate imaging lenses, e.g., objectives 27 and 28, is shown in FIG. 2, wherein only the principal beams are shown. Also, in this embodiment form of the invention a closure 29 with an opening 30 and 31 associated with each beam path is provided in the intermediate image plane 18 or in the vicinity thereof. As is shown in FIG. 2, opening 30 is associated with measurement beam path 3 and opening 31 is associated with reference beam path 4. In this construction, the closure 29 is also switchable so that the measurement beam path 3 and the reference beam path 4 can be interrupted. This switching capability is indicated by the double arrow 32 and can be carried out by displacement or rotation of the closure 29. The rest of the reference numbers shown in FIG. 2 refer to the same structural component parts as in FIG. 1.

Figure 3:
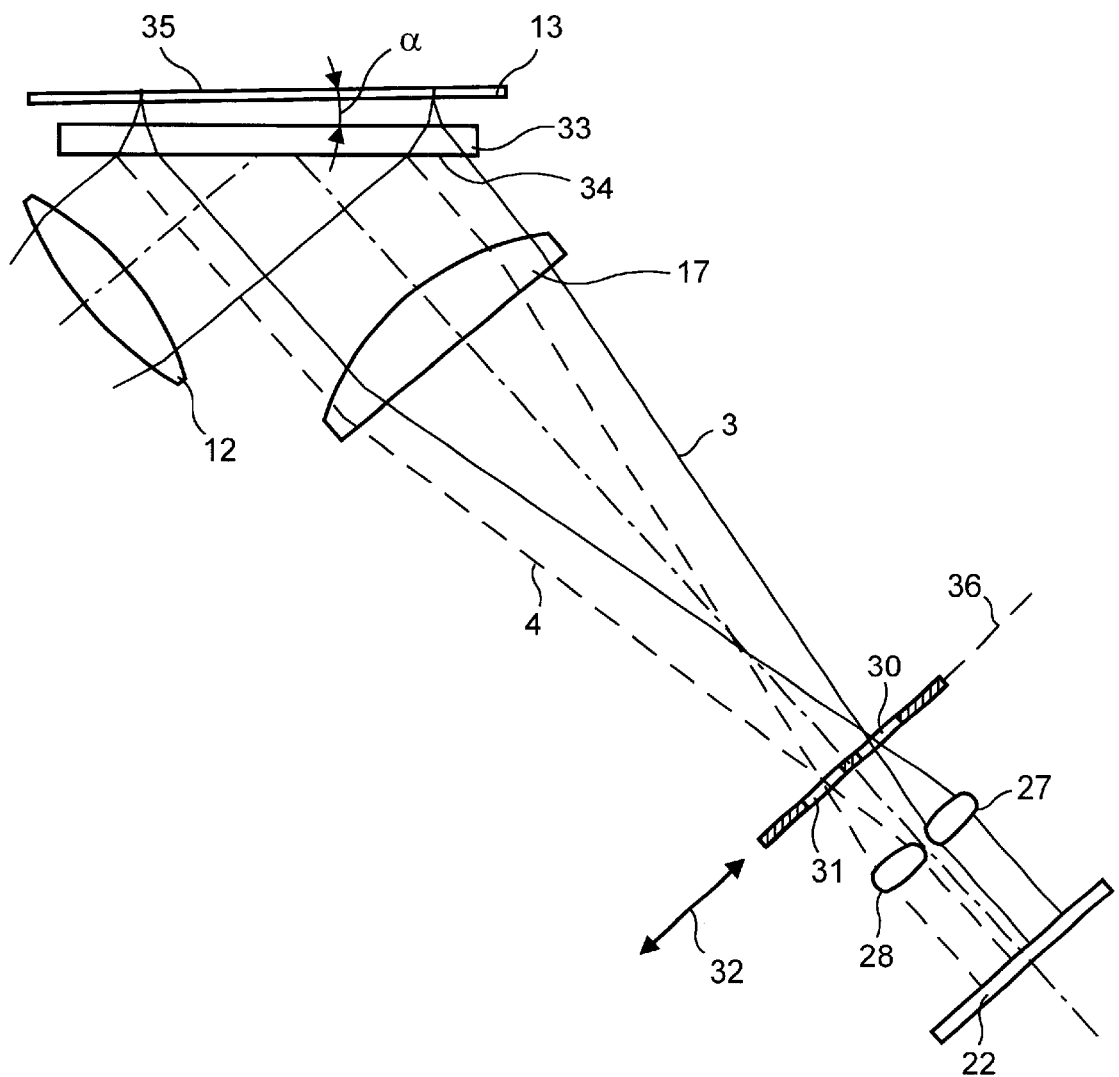
FIG. 3 shows an arrangement with a plane-parallel plate as splitter plate.

FIG. 3, in which the same reference numbers also identify structural component parts having the same function, shows an embodiment form of the invention in which the splitter plate is constructed as a plane-parallel plate 33. The beam splitting is carried out at the surface 34 of this plane-parallel plate 33 which is arranged at an angle a to the microtiter plate or specimen plate 13 carrying the specimens (not shown). The reference beam path 4 is generated by means of reflection at the surface 34. The light passing this surface 34 is reflected at the surface 35 of the specimen plate 13 carrying the specimens and forms the measurement beam path 3. The measurement beam path 3 and reference beam path 4 are separated from one another in an aperture diaphragm plane 36 in that the specimen plate 13 and plane-parallel plate 33 are inclined relative to one another by angle a. The measurement beam path 3 and the reference beam path 4 are imaged on the detector array 22 so as to be spatially separated from one another, but simultaneously, through the objectives 27; 28.

FIG. 4 shows the beam path of an arrangement according to the invention in which reflectors with curved and/or plane reflection surfaces are provided as imaging optical elements. In the beam paths of measurement beam path 3 and reference beam path 4 shown in FIG. 4, only the principal beams are shown for the sake of simplicity and clarity. As was already described in connection with the other drawings, the reference beam path 4 is generated in this arrangement by means of reflection at the splitter plate 14 from the light bundle of the illumination beam path 1 coming from the light source, not shown. The measurement beam path 3 is generated by means of reflection at the surface 16 of the specimen plate 13 which faces the specimens and communicates therewith via a carrier layer, not shown.

The measurement beam path 3 and reference beam path 4 are imaged at different positions 45; 46 on the detector array 22 simultaneously but so as to be spatially separated from one another by an imaging reflector 40 which is shown as a concave mirror and a reflector system 47 formed of additional reflectors 42; 43; 44. As is further shown in FIG. 4, reflector 42 is associated with measurement beam path 3 and reflector 43 is associated with reference beam path 4, wherein each of these two reflectors 42 and 43 directs the light impinging on them to a reflector 44 which is provided with plane or curved reflection surfaces, this light being directed to the detector array 22 proceeding from reflector 44; as in the construction according to FIG. 1, the detector array 22 is again connected with the computer 23 for further processing of the signals generated by the CCD elements of the detector array 22.

In this part of the beam path, the closure 29 is arranged between the reflector 40 and the reflector system 47 in, or in the vicinity of, an aperture diaphragm plane 41 for interrupting or releasing the measurement beam path 3 and reference beam path 4. The adjustment possibility of the closure 29 is illustrated by the double arrow 32.

Short-term and long-term fluctuations in the light source 5 are extensively eliminated with the arrangement according to the invention by means of simultaneous imaging of the beam components impinging and reflected on the specimen and of beam components of the reference beam path on the receiver array 22. In this way, requirements for referencing under conditions which are as identical as possible in the measurement beam path 3 and reference beam path 4 are met to a very great extent. The referencing shown in this case is identical with respect to wavelength, specimen location, beam direction, aperture and also time.

While the foregoing description and drawings represent the preferred embodiments of the present invention, it will be obvious to those skilled in the art that various changes and modifications may be made therein without departing from the true spirit and scope of the present invention.

What is claimed is:

1. An arrangement for the detection of biomolecular reactions and interactions using the RS screening method, comprising:

a specimen plate or microtiter plate for receiving the specimen to be examined;

a white light source with subsequently arranged illumination beam path for illuminating the specimen;

a splitter plate on which the specimen plate or the microtiter plate is set for generating a detection beam path formed of the measurement beam path and reference beam path;

a monochromator which comprises a plurality of interference filters and which is arranged subsequent to the light source in the illumination beam path;

a component assembly which collimates the illumination beam path, being formed of optical elements and being arranged between the monochromator and the specimen plate or microtiter plate;

a first optical imaging element for spatial separation of the measurement beam path and reference beam path in, or in the vicinity of, an intermediate image plane or aperture diaphragm plane of the detection beam path; and a second optical imaging element for imaging the measurement beam path and the reference beam path at different positions on a spatially resolving detector array of a CCD camera simultaneously and without overlap.

2. The arrangement according to claim 1, further comprising a switchable closure arranged in, or in the vicinity of, the intermediate image plane or aperture diaphragm plane.

3. The arrangement according to claim 1, wherein said second optical imaging element is arranged in, or in the vicinity of, the aperture diaphragm plane of the detector beam path.

4. The arrangement according to claim 1, wherein the second optical imaging element includes a separate imaging lens provided in the aperture diaphragm plane for each of the measurement beam path and for the reference beam path, respectively, for imaging these beam paths on the spatially resolving detector array of the CCD camera.

5. The arrangement according to claim 1, wherein the second optical imaging element includes a shared optical imaging system provided for spatially separate imaging of the measurement beam path and reference beam path on the detector array, wherein the first optical imaging element includes at least one deflecting prism arranged prior to the intermediate image plane or aperture diaphragm plane in the direction of light in each of the beam paths.

6. The arrangement according to claim 1, wherein the monochromator comprises a switchable filter disk carrying said plurality of interference filters.

7. The arrangement according to claim 1, wherein the splitter plate includes a wedge-shaped splitter plate, whose at least one optically active surface has at least one antireflection coating.

8. The arrangement according to claim 1, wherein the splitter plate includes a plane-parallel plate, wherein the plane-parallel plate encloses an angle $\alpha$ with the specimen plate or microtiter plate, wherein at least one optically active surface of the splitter plate has at least one antireflection coating.

9. The arrangement according to claim 1, wherein the component assembly and the second optical imaging element and/or the first optical imaging element are comprised of imaging reflectors.

10. The arrangement according to claim 9, wherein the second optical imaging element and/or the first optical imaging element are comprised of convex and concave and/or plane reflectors.

11. An apparatus for detection of biomolecular reactions and interactions using reflectometric interference spectroscopy, comprising:
   a first plate that receives a specimen;
   a light source that illuminates the specimen;
   a splitter plate disposed near the first plate, the splitter and first plates generating a measurement beam path and a reference beam path;
   a first optical imaging element that spatially separates the measurement and reference beam paths;
   a detector array; and
   a second optical imaging element that images simultaneously and without overlap both the measurement and reference beam paths at different positions on the detector array.

12. The apparatus according to claim 11, further comprising a switchable shutter operable to simultaneously block the reference and measurement beam paths from reaching the detector array.

13. The apparatus according to claim 11, wherein the second optical imaging element includes:
   a first objective for imaging the reference beam path on the detector array; and
   a second objective for imaging the measurement beam path on the detector array, the second objective being different from the first objective.

14. The apparatus according to claim 11, further comprising a monochromator disposed between the light source and the first plate.

15. The apparatus according to claim 14, wherein the monochromator includes a switchable filter disk carrying a plurality of interference filters.

* * * * *